(12) United States Patent
Sanghvi et al.

(10) Patent No.: US 8,038,631 B1
(45) Date of Patent: Oct. 18, 2011

(54) LAPAROSCOPIC HIFU PROBE

(76) Inventors: Narendra T. Sanghvi, Indianapolis, IN (US); Ralf Seip, Indianapolis, IN (US); Paul W. Mikus, Coto de Caza, CA (US); Dan Voic, Cedar Grove, NJ (US); Russell J. Fedewa, Indianapolis, IN (US); Roy F. Carlson, New Palestine, IN (US); Wo-Hsing Chen, Fishers, IN (US); Artur P. Katny, Ingalls, IN (US)

( * ) Notice: Subject to any disclaimer, the term of this patent is extended or adjusted under 35 U.S.C. 154(b) by 0 days.

(21) Appl. No.: 12/380,810

(22) Filed: Mar. 3, 2009

Related U.S. Application Data

(63) Continuation of application No. 11/445,004, filed on Jun. 1, 2006, now abandoned.

(60) Provisional application No. 60/686,499, filed on Jun. 1, 2005.

(51) Int. Cl.
*A61H 1/00* (2006.01)
*A61B 8/00* (2006.01)
*A61B 8/14* (2006.01)

(52) U.S. Cl. .............................. 601/2; 600/439; 600/459

(58) Field of Classification Search .................. 601/2–4; 600/439, 459; 606/27; 607/96
See application file for complete search history.

(56) References Cited

U.S. PATENT DOCUMENTS

| | | |
|---|---|---|
| 4,005,382 A | 1/1977 | Beaver |
| 4,074,564 A | 2/1978 | Anderson |
| 4,084,582 A | 4/1978 | Nigam |
| 4,161,121 A | 7/1979 | Zitelli et al. |
| 4,183,249 A | 1/1980 | Anderson |
| 4,207,901 A | 6/1980 | Nigam |
| 4,209,706 A | 6/1980 | Nunan |
| 4,223,560 A | 9/1980 | Glenn |
| 4,227,417 A | 10/1980 | Glenn |
| 4,231,373 A | 11/1980 | Waxman et al. |
| 4,241,412 A | 12/1980 | Swain |
| 4,241,610 A | 12/1980 | Anderson |
| 4,248,090 A | 2/1981 | Glenn |
| 4,257,271 A | 3/1981 | Glenn |
| 4,274,422 A | 6/1981 | Anderson et al. |
| 4,290,310 A | 9/1981 | Anderson |
| 4,317,370 A | 3/1982 | Glenn |
| 4,324,258 A | 4/1982 | Huebscher et al. |
| 4,325,381 A | 4/1982 | Glenn |
| 4,327,738 A | 5/1982 | Green et al. |
| 4,341,120 A | 7/1982 | Anderson |
| 4,378,596 A | 3/1983 | Clark |
| 4,407,293 A | 10/1983 | Suarez et al. |

(Continued)

FOREIGN PATENT DOCUMENTS

CA  1332441  10/1994

(Continued)

OTHER PUBLICATIONS

J.C. Rewcastle, Ph.D., "High Intensity Focused Ultrasound for Prostate Cancer: 2006 Technology and Outcome Update", Whitepaper, 2006, 14 pgs.

(Continued)

*Primary Examiner* — Michael T Rozanski
(74) *Attorney, Agent, or Firm* — William J. McNichol, Jr.; Reed Smtih LLP

(57) ABSTRACT

A high-intensity focused ultrasound ablation of tissue using minimally invasive medical procedures is provided.

10 Claims, 9 Drawing Sheets

U.S. PATENT DOCUMENTS

| | | | |
|---|---|---|---|
| 4,410,826 A | 10/1983 | Waxman et al. |
| 4,413,630 A | 11/1983 | Anderson et al. |
| 4,449,199 A | 5/1984 | Daigle |
| 4,530,358 A | 7/1985 | Forssmann et al. |
| 4,586,512 A | 5/1986 | Do-huu et al. |
| 4,620,546 A | 11/1986 | Aida et al. |
| 4,638,436 A | 1/1987 | Badger et al. |
| 4,658,828 A | 4/1987 | Dory |
| 4,664,121 A | 5/1987 | Sanghvi et al. |
| 4,807,633 A | 2/1989 | Fry |
| 4,858,613 A | 8/1989 | Fry et al. |
| 4,917,096 A | 4/1990 | Englehard et al. |
| 4,945,898 A | 8/1990 | Pell et al. |
| 4,951,653 A | 8/1990 | Fry et al. |
| 4,955,365 A | 9/1990 | Fry et al. |
| 5,033,456 A | 7/1991 | Pell et al. |
| 5,036,855 A | 8/1991 | Fry et al. |
| 5,054,470 A | 10/1991 | Fry et al. |
| 5,065,761 A | 11/1991 | Pell |
| 5,080,102 A | 1/1992 | Dory et al. |
| 5,117,832 A | 6/1992 | Sanghvi et al. |
| 5,134,988 A | 8/1992 | Pell et al. |
| 5,149,319 A | 9/1992 | Unger |
| 5,195,509 A | 3/1993 | Rentschler et al. |
| 5,215,680 A | 6/1993 | D'Arrigo |
| 5,219,401 A | 6/1993 | Cathignol et al. |
| 5,247,935 A | 9/1993 | Cline et al. |
| 5,295,484 A | 3/1994 | Marcus et al. |
| 5,316,000 A | 5/1994 | Chapelon et al. |
| 5,391,197 A | 2/1995 | Burdette et al. |
| 5,409,002 A | 4/1995 | Pell |
| 5,409,006 A | 4/1995 | Buchholtz et al. |
| 5,443,069 A | 8/1995 | Schaetzle |
| 5,470,350 A | 11/1995 | Buchholtz et al. |
| 5,492,126 A | 2/1996 | Hennige et al. |
| 5,520,188 A | 5/1996 | Hennige et al. |
| 5,573,497 A | 11/1996 | Chapelon |
| 5,601,526 A | 2/1997 | Chapelon et al. |
| 5,620,479 A | 4/1997 | Diederich |
| 5,630,837 A | 5/1997 | Crowley |
| 5,643,179 A | 7/1997 | Fujimoto et al. |
| 5,676,692 A | 10/1997 | Sanghvi et al. |
| 5,722,411 A | 3/1998 | Suzuki et al. |
| 5,725,482 A | 3/1998 | Bishop |
| 5,762,066 A | 6/1998 | Law et al. |
| 5,769,790 A | 6/1998 | Watkins et al. |
| 5,817,021 A | 10/1998 | Reichenberger |
| 5,840,031 A | 11/1998 | Crowley |
| 5,873,902 A | 2/1999 | Sanghvi et al. |
| 5,879,314 A | 3/1999 | Peterson et al. |
| 5,882,302 A | 3/1999 | Driscoll et al. |
| 5,906,580 A | 5/1999 | Kline-Schoder et al. |
| 5,993,389 A | 11/1999 | Driscoll et al. |
| 6,016,452 A | 1/2000 | Kasevich |
| 6,083,159 A | 7/2000 | Driscoll et al. |
| 6,093,883 A | 7/2000 | Sanghvi et al. |
| 6,126,619 A | 10/2000 | Peterson et al. |
| 6,217,530 B1 | 4/2001 | Martin et al. |
| 6,245,053 B1 | 6/2001 | Benjamin |
| 6,334,846 B1 | 1/2002 | Ishibashi et al. |
| 6,375,634 B1 | 4/2002 | Carroll |
| 6,425,867 B1 | 7/2002 | Vaezy et al. |
| 6,500,133 B2 | 12/2002 | Martin et al. |
| 6,575,956 B1 | 6/2003 | Brisken et al. |
| 6,618,620 B1 | 9/2003 | Freundlich et al. |
| 6,626,855 B1 | 9/2003 | Weng et al. |
| 6,656,136 B1 | 12/2003 | Weng et al. |
| 6,666,835 B2 | 12/2003 | Martin et al. |
| 6,676,601 B1 | 1/2004 | Lacoste et al. |
| 6,685,639 B1 | 2/2004 | Wang et al. |
| 6,685,640 B1 | 2/2004 | Fry et al. |
| 6,716,184 B2 | 4/2004 | Vaezy et al. |
| 6,733,457 B2 | 5/2004 | Flesch et al. |
| 6,772,490 B2 | 8/2004 | Toda |
| 6,812,204 B1 | 11/2004 | McHale et al. |
| 6,846,290 B2 | 1/2005 | Lizzi et al. |
| 6,875,176 B2 | 4/2005 | Mourad et al. |
| 2001/0008758 A1 | 7/2001 | McHale et al. |
| 2001/0014780 A1 | 8/2001 | Martin et al. |
| 2002/0035361 A1 | 3/2002 | Houser et al. |
| 2002/0095087 A1 | 7/2002 | Mourad et al. |
| 2002/0102216 A1 | 8/2002 | Lanza et al. |
| 2002/0193785 A1 | 12/2002 | Naghavi et al. |
| 2003/0018358 A1 | 1/2003 | Saadat |
| 2003/0028111 A1 | 2/2003 | Vaezy et al. |
| 2003/0040698 A1 | 2/2003 | Makin et al. |
| 2003/0060736 A1 | 3/2003 | Martin et al. |
| 2003/0171700 A1 | 9/2003 | Martin et al. |
| 2003/0191396 A1 | 10/2003 | Sanghvi et al. |
| 2003/0204141 A1 | 10/2003 | Nock et al. |
| 2003/0229331 A1 | 12/2003 | Brisken et al. |
| 2004/0030227 A1 | 2/2004 | Littrup et al. |
| 2004/0030268 A1 | 2/2004 | Weng et al. |
| 2004/0039312 A1 | 2/2004 | Hillstead et al. |
| 2004/0059220 A1 | 3/2004 | Mourad et al. |
| 2004/0071664 A1 | 4/2004 | McHale et al. |
| 2004/0106870 A1 | 6/2004 | Mast |
| 2004/0106880 A1 | 6/2004 | Weng et al. |
| 2004/0133192 A1 | 7/2004 | Houser et al. |
| 2004/0167403 A1 | 8/2004 | Nightingale et al. |
| 2004/0210289 A1 | 10/2004 | Wang et al. |
| 2004/0254419 A1 | 12/2004 | Wang et al. |
| 2004/0264293 A1 | 12/2004 | Laugharn et al. |
| 2005/0015009 A1 | 1/2005 | Mourad et al. |
| 2005/0025797 A1 | 2/2005 | Wang et al. |
| 2005/0038340 A1 | 2/2005 | Vaezy et al. |
| 2005/0043626 A1 | 2/2005 | Marciante et al. |
| 2005/0074407 A1 | 4/2005 | Smith |
| 2005/0154308 A1 | 7/2005 | Quistgaard et al. |
| 2005/0154309 A1 | 7/2005 | Etchells et al. |
| 2005/0154431 A1 | 7/2005 | Quistgaard et al. |
| 2005/0193451 A1 | 9/2005 | Quistgaard et al. |
| 2006/0293598 A1* | 12/2006 | Fraser .................. 600/439 |

FOREIGN PATENT DOCUMENTS

| | | |
|---|---|---|
| CA | 1338240 | 4/1996 |
| CA | 2250081 | 9/1998 |
| EP | 0596513 | 11/1994 |
| WO | 9316641 | 9/1993 |
| WO | 9747881 | 12/1997 |
| WO | 9858588 | 12/1998 |
| WO | 9949788 | 10/1999 |
| WO | 0128623 | 4/2001 |
| WO | 0182777 | 11/2001 |
| WO | 0182778 | 11/2001 |
| WO | 0224050 | 3/2002 |
| WO | 2005107601 | 11/2005 |

OTHER PUBLICATIONS

HIFU Technology Pte. Ltd., The Haifu Knife Model-JC Focused Ultrasound Tumor Therapeutic System, updated, 1 page.

R. Seip et al., "Sonablate 500: A Novel Platform for Transrectal Image-Guided HIFU Treatment of Localized Prostate Cancer," presented at the 32nd Annual Symposium of the Ultrasonic Industry Association (UIA), Oct. 2002, 28 pgs.

T. Uchida, et al., "Clinical Outcome of High-Intensity Focused Ultrasound (HIFU) for the Treatment of Localized Prostate Cancer: 5-Years Experience", to appear in the Proc. of the International Symposium on Therapeutic Ultrasound, 2004, 1 pg. (Abstract).

J.S. Tan, et al., "Design of Focused Ultrasound Phased Arrays for Prostate Treatment," IEEE Ultrasonics Symposium Proceedings, Puerto Rico, 2000, 5 pgs.

T. Gardner, et al., "HIFU Prostatectomy for Prostate Cancer: The USA Experience", to appear in the Proc. of the International Symposium on Therapeutic Ultrasound, 2003, 1 pg. (Abstract).

J.C. Rewcastle, Ph.D., "High Intensity Focused Ultrasound for Prostate Cancer: Clinical Results and Technical Evolution", Whitepaper, 2004, 14 pgs.

T. Uchida, et al., "Transrectal High-Intensity Focused Ultrasound for Treatment of Patients with Stage T1b-2N0M0 Localized Prostate Cancer: A Preliminary Report", Japanese Journal of Endourology and ESWL, vol. 16, pp. 108-114, 2003.

T. Uchida, et al., "Transrectal High-Intensity Focused Ultrasound for Treatment of Patients with Stage T1b-2N0M0 Localized Prostate Cancer: A Preliminary Report", Urology, 2002, pp. 394-399.

T. Uchida et al., "Transrectal High Intensity Focused Ultrasound for the Treatment of Localized Prostate Cancer," International Symposium on Therapeutic Ultrasound, Seattle, 2002, 9 pgs.

S. Madersbacher, et al., "Effect of High-Intensity Focused Ultrasound on Human Prostate Cancer in Vivo", Cancer Research 55, Aug. 1995, pp. 3346-3351.

N. T. Sanghvi, et al., "Noninvasive Surgery of Prostate Tissue by High Intensity Focused Ultrasound: An Updated Report", European Journal of Ultrasound, vol. 9; 1999, pp. 19-29.

T. Uchida, et al., "Clinical Outcome of High-Intensity Focused Ultrasound for Treating Benign Prostatic Hyperplasia: Preliminary Report," Urology, 1998, pp. 66-71.

L. D. Sullivan, et al., "Early Experience with High-Intensity Focused Ultrasound for the Treatment of Benign Prostatic Hypertrophy", British Journal of Urology, 79; 1997, pp. 172-176.

N. T. Sanghvi, et al., "Noninvasive Surgery of Prostate Tissue by High-Intensity Focused Ultrasound", IEEE Transactions on Ultrasonics, Ferroelectrics, and Frequency Control. vol. 43, No. 6, Nov. 1996, pp. 1099-1110.

S. Madersbacher, et al., "High-Intensity Focused Ultrasound in Urology", Japanese journal of Endourology and ESWL, vol. 9, No. 1, 1996, pp. 5-15.

F. Fry, et al., "Ultrasound and Microbubbles: Their Generation, Detection and Potential Utilization in Tissue and Organ Therapy—Experimental", Ultrasound in Medicine & Biology, vol. 21, No. 9, 1995, pp. 1227-1237.

S. Madersbacher, et al., "Tissue Ablation in Benign Prostatic Hyperplasia with High Intensity Focused Ultrasound", J. Urology, vol. 152, Dec. 1994, pp. 1956-1961.

R. S. Foster, et al., "High-Intensity Focused Ultrasound for the Treatment of Benign Prostatic Hypertrophy", Seminars in Urology, vol. XII, No. 3, pp. 200-204, Aug. 1994.

S. Umemura, et al., "Coagulation of Swine Liver and Canine Prostate with a Protoype Split-Focus Transducer", IEEE Ultrasonics Symposium, 1999, 14 pgs.

J. Wu, et al., "Experimental Studies of Using a Split Beam Transducer for Prostate Cancer Therapy in Comparison to Single Beam Transducer", IEEE Ultrasonics Symposium, 1999, 4 pgs.

T. Uchida, "Localized Prostate Cancer Treatment with HIFU", Translated and updated from the Journal of Highly Advanced Medical Technology, vol. 15 Mar. 2000, 1 pg.

R. Seip, et al., "Comparison of Split-Beam Transducer Geometries and Excitation Configurations for Transrectal Prostate HIFU Treatments", IEEE Ultrasonics Symposium Proceedings, 2001, 4 pgs.

R. Seip et al., "High-Intensity Focused Ultrasound (HIFU) Phased Arrays: Recent Developments in Transrectal Transducers and Driving Electronics Design," Third International Symposium on Therapeutic Ultrasound, Lyon, France, Jun. 2003, 6 pgs.

R. Seip et al., "High-Intensity Focused Ultrasound (HIFU) Phased Arrays: Recent Developments in Transrectal Transducers and Driving Electronics Design," Third International Symposium on Therapeutic Ultrasound, Lyon, France, Jun. 2003, (Poster).

K. Ishida et al., "Development and animal experiment of variable focusing HIFU system for prostate cancer treatment," Proc. of the International Symposium on Therapeutic Ultrasound, 2003, 6 pgs.

K. Ishida et al., "Development and animal experiment of variable focusing HIFU system for prostate cancer treatment," Proc. of the International Symposium on Therapeutic Ultrasound, 2003, 18 pgs.

R. Seip, et al., "Annular and Cylindrical Phased Array Geometries for Transrectal High-Intensity Focused Ultrasound (HIFU) using PZT and Piezocomposite Materials," ISTU 4 Conference, Oct. 2004, Kyoto, Japan, 3 pgs.

R. Seip, et al., "High-Intensity Focused Ultrasound (HIFU) Multiple Lesion Imaging: Comparison of Detection Algorithms for Real-Time Treatment Control," IEEE Ultrasonics Symposium Proceedings, Munich, Germany, 2002, pp. 1395-1398.

R. Seip et al., "Real-time Detection of Multiple Lesions during High Intensity Focused Ultrasound (HIFU) Treatments," International Symposium on Therapeutic Ultrasound, 2002, 8 pgs.

N.T. Sanghvi, et al., "Decision Theory Applied to High-Intensity Focused Ultrasound (HIFU) Treatment Evaluation," 2003 AIUM Annual Meeting, Jun. 1-4, 2003, Montreal, Quebec, Canada, 24 pgs.

W. Chen, et al., "The Detection and Exclusion of Prostate Neuro-Vascular Bundle (NVB) in Automated HIFU Treatment Planning Using a Pulsed-Wave Doppler Ultrasound System," 2004 ISTU Conference, Kyoto, Japan, 3 pgs.

R. Seip, et al., "Transurethral High Intensity Focused Ultrasound: Catheter Based Prototypes and Experimental Results," IEEE Ultrasonics Symposium Proceedings, Puerto Rico, 2000, 4 pgs.

J. Tavakkoli, et al., "A Laparoscopic HIFU Probe for Kidney Ablation Prior to Partial Nephrectomy," IEEE Ultrasonics Symposium Proceedings, Atlanta, 2001, 4 pgs.

N.T. Sanghvi, et al., "Laparoscopically Delivered HIFU for Partial Renal Ablation," 17th International Congress on Acoustics, Sep. 2-7, 2001, Rome, Italy 2 pgs.

J. Tavakkoli, et al., "Laparoscopic High Intensity Focused Ultrasound: Application to Kidney Ablation," International Symposium on Therapeutic Ultrasound, Seattle, 2002, 9 pgs.

J. Tavakkoli, et al., "A Laparoscopic HIFU Probe with Integrated Phased Array Ultrasound Imaging," Third International Symposium on Therapeutic Ultrasound, Jun. 2003, Lyon, France, 6 pgs.

J. Tavakkoli, et al., "A Laparoscopic HIFU Probe with Integrated Phased Array Ultrasound Imaging," International Symposium on Therapeutic Ultrasound, 2003. (Poster).

R. Seip, et al., "Automated HIFU Treatment Planning and Execution based on 3D Modeling of the Prostate, Urethra, and Rectal Wall", 2004 IEEE Ultrasonics Symposium Proceedings, 4 pgs.

R. Seip, et al., "Automated HIFU Treatment Planning and Execution based on 3D Modeling of the Prostate, Urethra, and Rectal Wall", 2004 IEEE Ultrasonics Symposium Proceedings. (Poster).

J.S. Tan, et al., "Ultrasound Phased Arrays for Prostate Treatment", J. Acoust. Soc. Am., vol. 109, No. 6, Jun. 2001, pp. 3055-3064.

R. Seip, et al., "Feasibility Study for the Treatment of Brachytherapy Failure Prostate Caner using High-Intensity Focused Ultrasound," Third International Symposium on Therapeutic Ultrasound, Lyon, France, Jun. 2003, 6 pgs.

M. Bailey, et al., "Caviation Detection and Suppression in HIFU," Proc. of the International Symposium on Therapeutic Ultrasound, 2003, 1 pg. (Poster).

The American Society for Therapeutic Radiology and Oncology Consensus Panel, "Consensus Statement: Guidelines for PSA Following Radiation Therapy," Int J. Radiation Oncology Biol. Phys., vol. 37, No. 5, 1997, pp. 1035-1041.

N.T. Sanghvi, et al., "Total Prostate Ablation for the Treatment of Localized Prostate Cancer Using Image Guided HIFU," presented at the 2002 IEEE Ultrasonics Symposium. (Poster).

* cited by examiner

LAPAROSCOPIC HIFU PROBE

This application is a continuation of U.S. application Ser. No. 11/445,004 filed on Jun. 1, 2006, now abandoned which claims the benefit of U.S. Provisional Application No. 60/686,499 filed on Jun. 1, 2005. The contents of 11/445,004 and 60/686,499 are expressly incorporated by reference herein.

BACKGROUND AND SUMMARY OF THE INVENTION

The present invention relates to instruments to conduct minimally invasive medical procedures with the aid of laparoscopic techniques, and to such procedures themselves. More particularly, the present invention relates to high-intensity focused ultrasound ablation of tissue using minimally invasive medical procedures.

Several minimally invasive and non-invasive techniques for the treatment of living tissues and organs with ultrasound, including high-intensity, focused ultrasound, sometimes referred to hereinafter as HIFU, are known. There are, for example, the techniques and apparatus described in U.S. Pat. Nos. 4,084,582; 4,207,901; 4,223,560; 4,227,417; 4,248,090; 4,257,271; 4,317,370; 4,325,381; 4,586,512; 4,620,546; 4,658,828; 4,664,121; 4,858,613; 4,951,653; 4,955,365; 5,036,855; 5,054,470; 5,080,102; 5,117,832; 5,149,319; 5,215,680; 5,219,401; 5,247,935; 5,295,484; 5,316,000; 5,391,197; 5,409,006; 5,443,069; 5,470,350; 5,492,126; 5,573,497; 5,601,526; 5,620,479; 5,630,837; 5,643,179; 5,676,692; 5,840,031. The disclosures of these references are hereby incorporated herein by reference.

HIFU Systems for the treatment of diseased tissue are known. An exemplary HIFU system is the Sonablate® 500 HIFU system available from Focus Surgery, Inc. located at 3940 Pendleton Way, Indianapolis, Ind. 46226. The Sonablate® 500 HIFU system uses a dual-element, confocal ultrasound transducer which is moved by mechanical methods, such as motors, under the control of a controller. Typically one element of the transducer is used for imaging and the other element of the transducer is used for providing HIFU Therapy.

Further details of suitable HIFU systems may be found in U.S. Pat. No. 5,762,066; U.S. Abandoned patent application Ser. No. 07/840,502 filed Feb. 21, 1992, Australian Patent No. 5,732,801; Canadian Patent No. 1,332,441; Canadian Patent No. 2,250,081; and U.S. Pat. No. 6,685,640, the disclosures of which are expressly incorporated by reference herein.

As used herein the term "HIFU Therapy" is defined as the provision of high intensity focused ultrasound to a portion of tissue. It should be understood that the transducer may have multiple foci and that HIFU Therapy is not limited to a single focus transducer, a single transducer type, or a single ultrasound frequency. As used herein the term "HIFU Treatment" is defined as the collection of one or more HIFU Therapies. A HIFU Treatment may be all of the HIFU Therapies administered or to be administered, or it may be a subset of the HIFU Therapies administered or to be administered. As used herein the term "HIFU System" is defined as a system that is at least capable of providing a HIFU Therapy.

The laparoscopic probe of an illustrated embodiment of the present invention is targeted for minimally invasive laparoscopic tissue treatments of the kidney and liver. The probe is light weight, easy to use, and adaptable to the current Sonablate® 500 HIFU system. The laparoscopic probe, with the Sonablate® 500 system, illustratively provides laparoscopic ultrasound imaging, treatment planning, treatment and monitoring in a single probe. The probe fits through a trocar (illustratively an 18 millimeter diameter trocar). A removable, sterile, and disposable probe tip includes a coupling bolus which covers the tip of the probe. The bolus is very thin and illustratively expands to about two or three times its size when water is introduced. This provides a water medium surrounding the probe which is needed for ultrasonic imaging and treatment. Cooling the transducer that provides the imaging and treatment is achieved through a sterile, distilled, degassed passive recirculating water system. The entire probe is ethylene oxide (EO) sterilizable, and the cooling system is gamma-sterilizable.

The laparoscopic probe of the present invention provides an alternative solution to invasive surgery. As a result, recovery time is reduced and hospital visits are considerably shorter. In addition the ablation provided by the laparoscopic probe permits the surgeon to target tissue without stopping the blood supply to the organ. For example, to perform a partial nephrectomy in a conventional manner, the surgeon illustratively shuts off the supply of blood to the kidney and has a limited amount of time to excise the targeted tissue, seal the blood vessels and restart the blood supply to the kidney. If the surgeon takes too long, damage to the kidney and possible organ death may occur. Thus being able to treat large and small volumes of tissue while permitting blood flow to the organ is a significant contribution.

Additional features of the present invention will become apparent to those skilled in the art upon consideration of the following detailed description of illustrative embodiments exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

Figure 1:
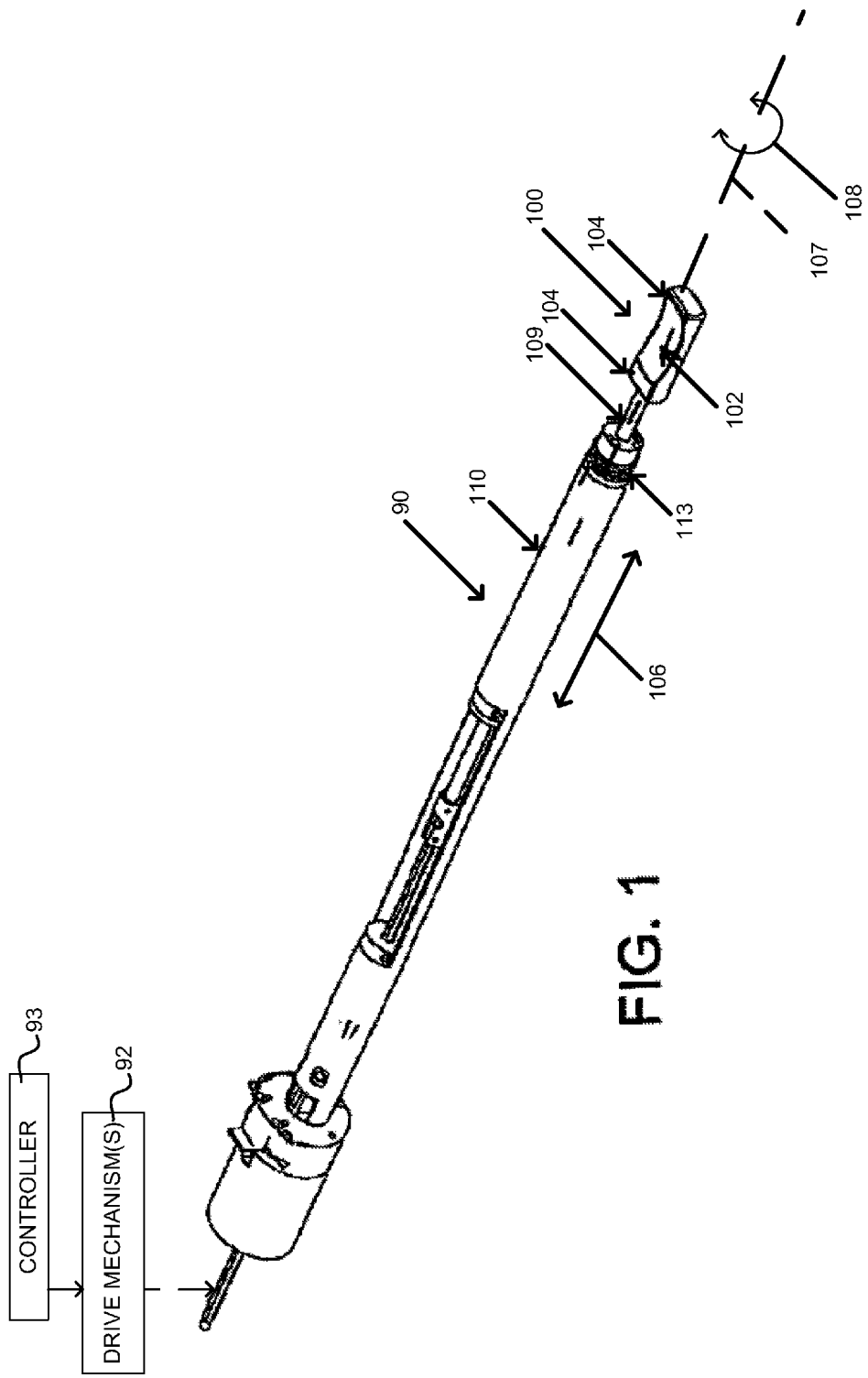
FIG. 1 is a perspective view of a portion of the laparoscopic probe of the present invention including a controller, a drive mechanism, and a movable transducer.

U.S. application Ser. No. 10/380,031, owned by Focus Surgery, Inc. located in Indianapolis, Ind., discloses a HIFU laparoscopic probe and minimally invasive treatment procedure. The '031 application is expressly incorporated by reference herein.

In an illustrated minimally invasive procedure as described in the '031 application, in a HIFU-based procedure for treatment of a kidney, the patient is first prepared. Next, three incisions are illustratively made on the abdomen below the diaphragm through trocars. The trocars are left in place, as is customary, to permit the sealing of the abdomen when instruments are passed through the seals of the trocars into the abdomen for the conduct of the procedure.

A laparoscope for providing visual observation of the surgical field is passed through one of the trocars. The laparoscope is conventionally coupled to a video camera and a light source for illuminating the surgical field and returning images to a surgical monitor. The laparoscope provides a pair of fiberoptic ports, one an output port for light from source to the surgical field, and one an input port for the returning image information to video camera. A second of the trocars provides, among other things, a passageway for the introduction into the abdomen of a relatively inert gas, such as, for example, carbon dioxide, from a source in order to permit the inflation of the abdomen below the diaphragm. This increases the space inside the abdomen for maneuvering surgical instruments including the laparoscope, and provides a clearer view of the surgical field.

The third trocar provides access through the abdominal wall and into the surgical field for a HIFU probe which is used to ablate the surgical site of a diseased kidney, for example, for the virtually bloodless ablation of (a) tumor(s) on the surface of, and/or within, the kidney. Should the surgical procedure call for it, additional trocars can, of course, be provided for passing into the body additional HIFU probes 90 to be used in conjunction with each other in an ablation procedure. If a tumor is difficult to visualize, a catheter may be used to permit the introduction into the surgical field of (an) ablation enhancing medium (media) and other media at (an) appropriate time(s) during the procedure. The same, or a different, medium (media) may also be introduced through the catheter to improve the accuracy of the targeting of the surgical site for ablation and provide feedback to the treating physician of the progress of the treatment. For example, lesions which are not on the surface of the tissue being treated are not easily visible, or in many cases visible at all, in the laparoscopically informed monitor.

In order to provide feedback to the treating physician of the progress of treatment of a site not visible on the monitor, the ultrasound probe includes an ultrasound visualization capability. Additional mechanisms may be provided for essentially real-time monitoring of the progress of the treatment. For example, it is known in the ultrasound visualization and therapy arts that there are numerous mechanisms available to promote visualization of the progress of ultrasound treatment within an organ or tissue.

The probe is illustratively integrated into, or mounted to be manipulated by, a drive mechanism, and controlled, for example, by means of a joystick, keypad, touch screen, or any other appropriate control mechanism such as controller. Any of such mechanisms can incorporate feedback control, not only of a visual nature, provided via a laparoscope, but also of the ultrasound imaging type via probe.

As shown in FIG. 1, the probe 90 includes a segmented, curved rectangular elliptical transducer 100 of the general type described in, for example, WO 99/49788. The transducer 100 has a central segment 102 which is used both for visualization and therapy and outer segment(s) 104 which is (are) used for therapy, in accordance with known principles. However, it will immediately be appreciated that other single element or multi-segment transducer configurations, such as ones providing variable focal length, can be used to advantage in other embodiments of the invention. Some of such variable focal length configurations, and driving and receiving systems for them, are described in the prior art incorporated herein by reference.

The structure of the laparoscopic probe 90 is composed of two main components, the main body or frame, and the probe tip assembly 111. The frame illustratively provides a drive mechanism 92 for moving the transducer 100 back and forth in the direction of double headed arrow 106 in FIG. 1 (50 mm minimum movement), and also to rotate the transducer 100 about its axis 107 as illustrated by arrow 108. It is understood that other suitable drive mechanism(s) 92 may be used to move the transducer 100 (90° minimum rotation (+/−) 45°).

The probe tubing assembly 110 is primarily made from stainless steel. There are illustratively two bushings that guide the water tubing to the transducer as well as provide support for access to the coupling of the transducer shaft 109 and the hexagonal shaft. The transducer shaft 109 is coupled to the hex shaft (mentioned above) and is able to rotate and translate for both imaging and continuous HIFU Treatment.

Figure 2:
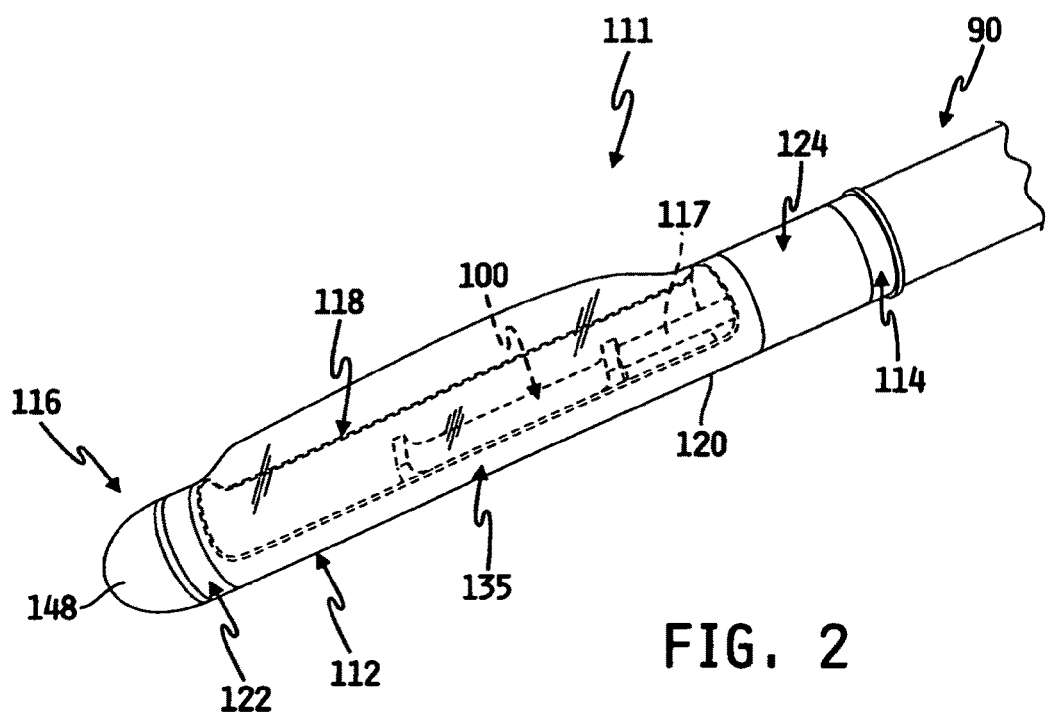
FIG. 2 is a perspective view of a removable probe tip assembly of the present invention including an expandable bolus for acoustically coupling the transducer to a targeted area and for cooling the transducer during the procedure.
Figure 3:
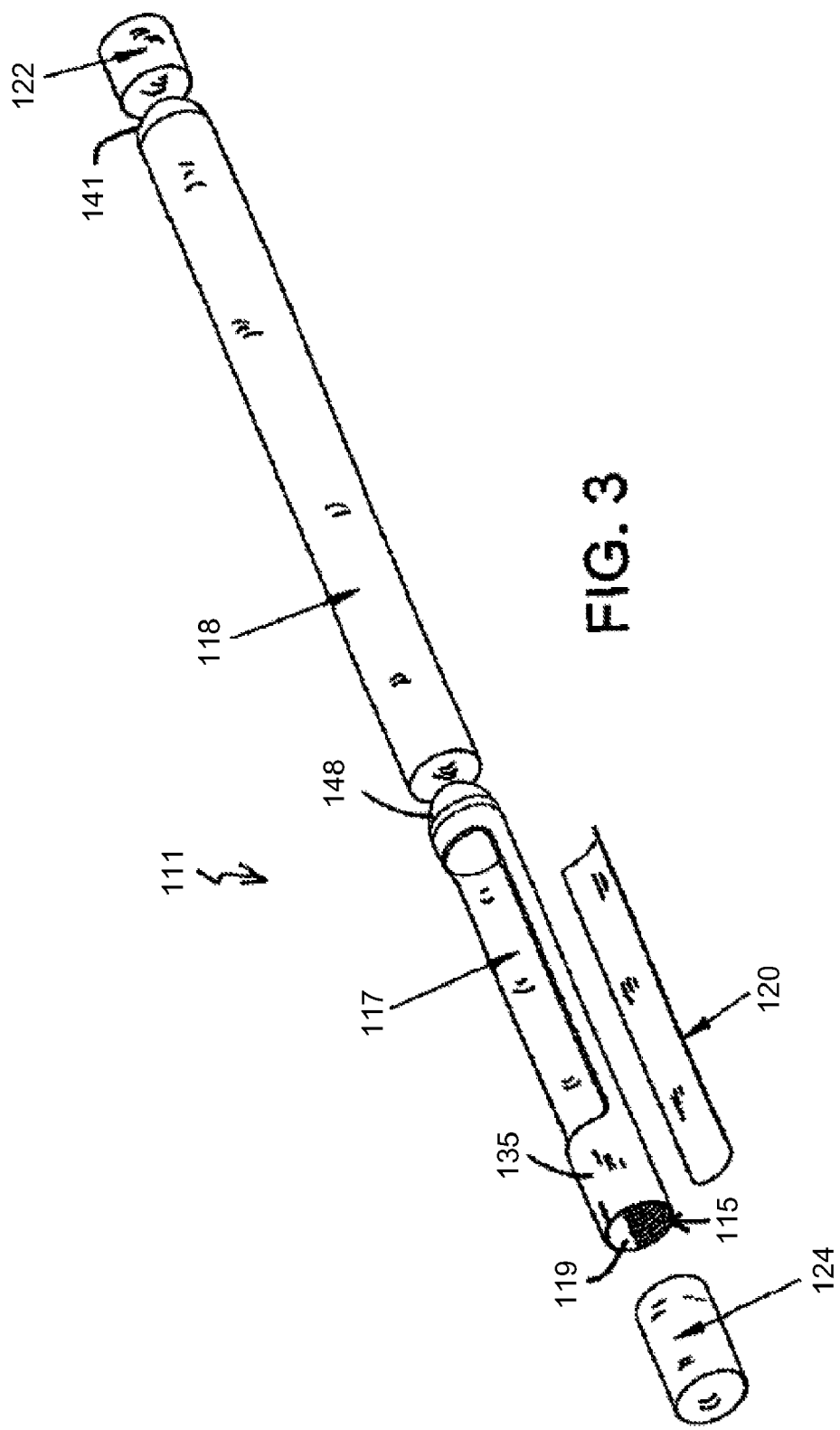
FIG. 3 is an exploded perspective view of the removable probe tip assembly of FIG. 2.
Figure 4:
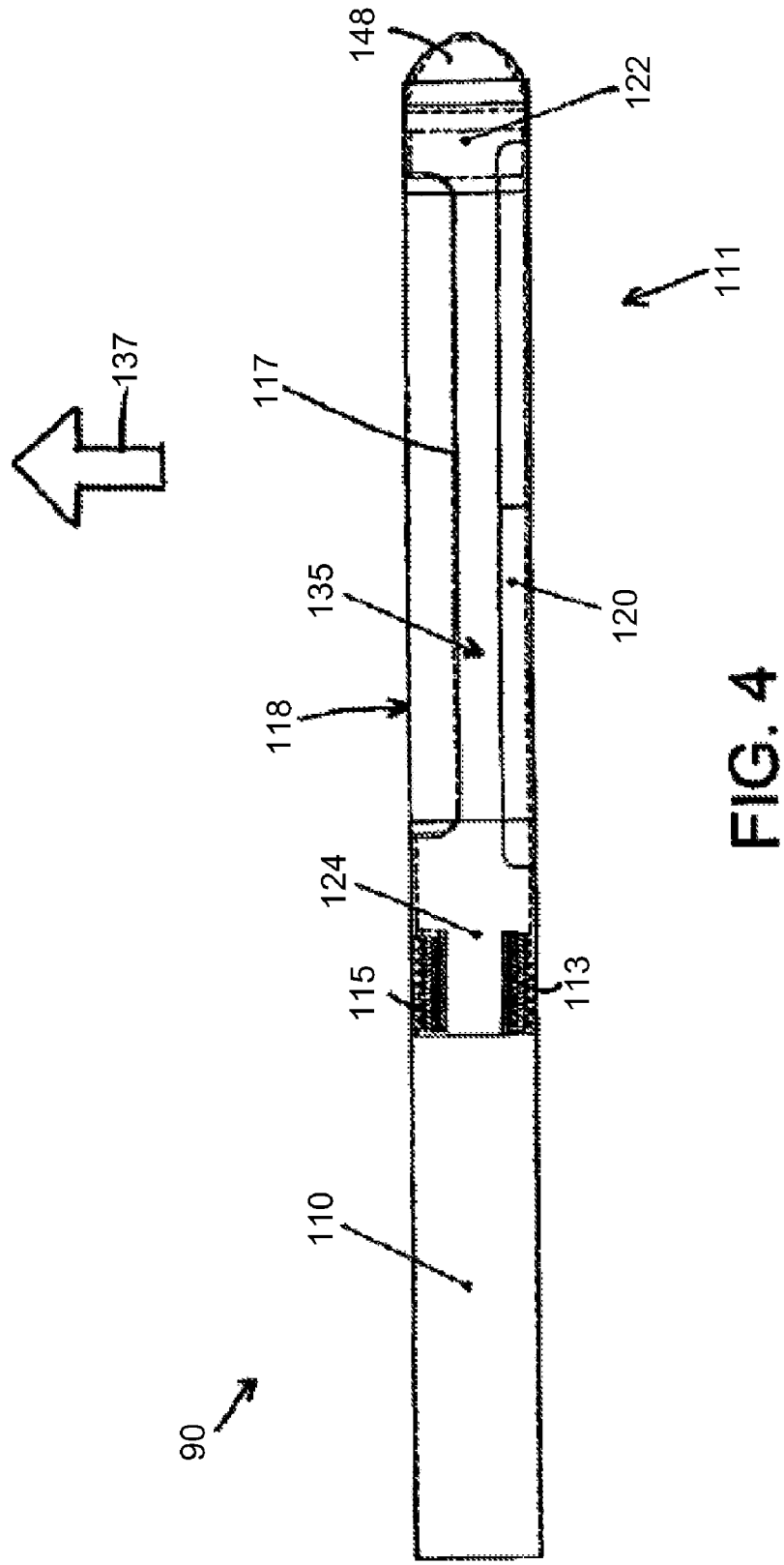
FIG. 4 is a side elevational view of the removable probe tip assembly of FIGS. 2 and 3.

The probe tip illustratively includes two components: a main stainless steel tubing body 110 shown in FIG. 1 which illustratively has a 17 mm diameter or less to fit into an 18 mm trocar, and a removable tip assembly 111 shown in FIGS. 2-4. The main tubing body 110 illustratively has a threaded end 113 that connects with threads formed in distal end 114 of the removable tip 111. The removable tip 111 also includes a distal end 116 having a rounded tip 148 coupled thereto. The internal threading 115 (best shown in FIG. 3) has the threads removed on opposite sides of the tubing (see area 119) to permit the transducer to pass into the tip. A coupling water bolus 118, a curved thin stainless steel shim material 120, and two short pieces of very thin heat shrink tubing 122, 124 complete the illustrated removable tip 111 components. The removable tip 111 is illustratively made from stainless steel but may be molded from a resin such as Ultem® resin or other suitable material. The bolus 118 is illustratively formed from a polyurethane membrane or condom inserted over the end of probe tip 111. Bolus 118 is illustratively a tubular membrane with a sealed end 141 best shown in FIG. 3. A shim 120 is then located over the bolus membrane 118 on an opposite side of a treatment aperture 117. Shim 120 is coupled to the tip 111 only by two heat shrinking tubes 122 and 124 best shown in FIGS. 3 and 4. Tubes 122 and 124 have a thickness of about 4-5 thousandths of an inch. Illustratively the membrane is made from HT-9 material available from Apex Medical. The heat shrink tubing is illustratively made from ultra thin polyester tubing and is made by Advanced Polymers. The removable tip assembly 111 is designed to be disposable (USP—Class VI) and sterile. Sterilizing the removable tip can be achieved via ethylene oxide (EO) sterilization or gamma sterilization.

The tubes 122 and 124 are very thin and facilitate insertion of the probe tip 111 through the trocar 60. Tubes 122 and 124 minimize the thickness of the tip 111 which is desirable for laparoscopic procedures. Additional adhesives or other securing means are not required to secure the shim 120 to the bolus 118 or tip 111.

As discussed above, the removable tip 111 includes a housing 135 formed to include an opening or aperture 117. The transducer 100 is movable within the aperture as controlled by the drive mechanism 92 and controller 93 to provide the HIFU Therapy. Transducer 100 is configured to emit ultrasound energy through the aperture 117 in the direction of arrow 137 which is referred to as a treatment direction.

The housing 135, the tubes 122, 124 and the shim 120 work together to cause the bolus 118 to expand only in the treatment direction 137 in FIG. 4. The shim 120 forces the bolus 118 to expand in the direction of the opening 117 in the removable tip 111 as shown in FIG. 2. The heat shrink tubes 122, 124 hold the shim 120 in the desired position as well as constraining the ends of the bolus membrane 118. The expansion of the water bolus 118 acoustically couples the ultrasound to the patient. It also changes the location of the transducer focus with respect to the target targeted area, thereby changing the position of the targeted tissue with respect to distance from the transducer 100.

As discussed above, the stainless steel shim 120 is an element used to control expansion of the water bolus 118 during a treatment. Removing the stainless steel shim 120 would result in a uniform expansion of the water bolus 118 around the probe tip 111 in the presence of no external objects. With no shim 120 applying pressure to hold the probe against tissue for treatment at a specific distance would result in the bolus 118 reacting by shifting water behind the probe tip and away from the tissue. This may result in a poor and uncontrolled acoustic coupling of the transducer 100 to the tissue and the inability to accurately place the HIFU Treatment zones in their desired locations.

The bolus membrane material 118 illustratively has a memory characteristic. This provides a substantially flat elevated position of bolus 118 above aperture 117 for uniform contact and coupling with a larger tissue area. Once the probe 90 is positioned within a body, a controller controls drive mechanisms to move the transducer 100 to provide HIFU Therapy.

Providing a sterile, distilled, degassed water recirculation system for cooling and acoustic coupling during treatment is another illustrated aspect of the present invention. The water should be sterile due to the required sterile surgical environment and degassed for the successful operation of the HIFU transducer.

Figure 6:
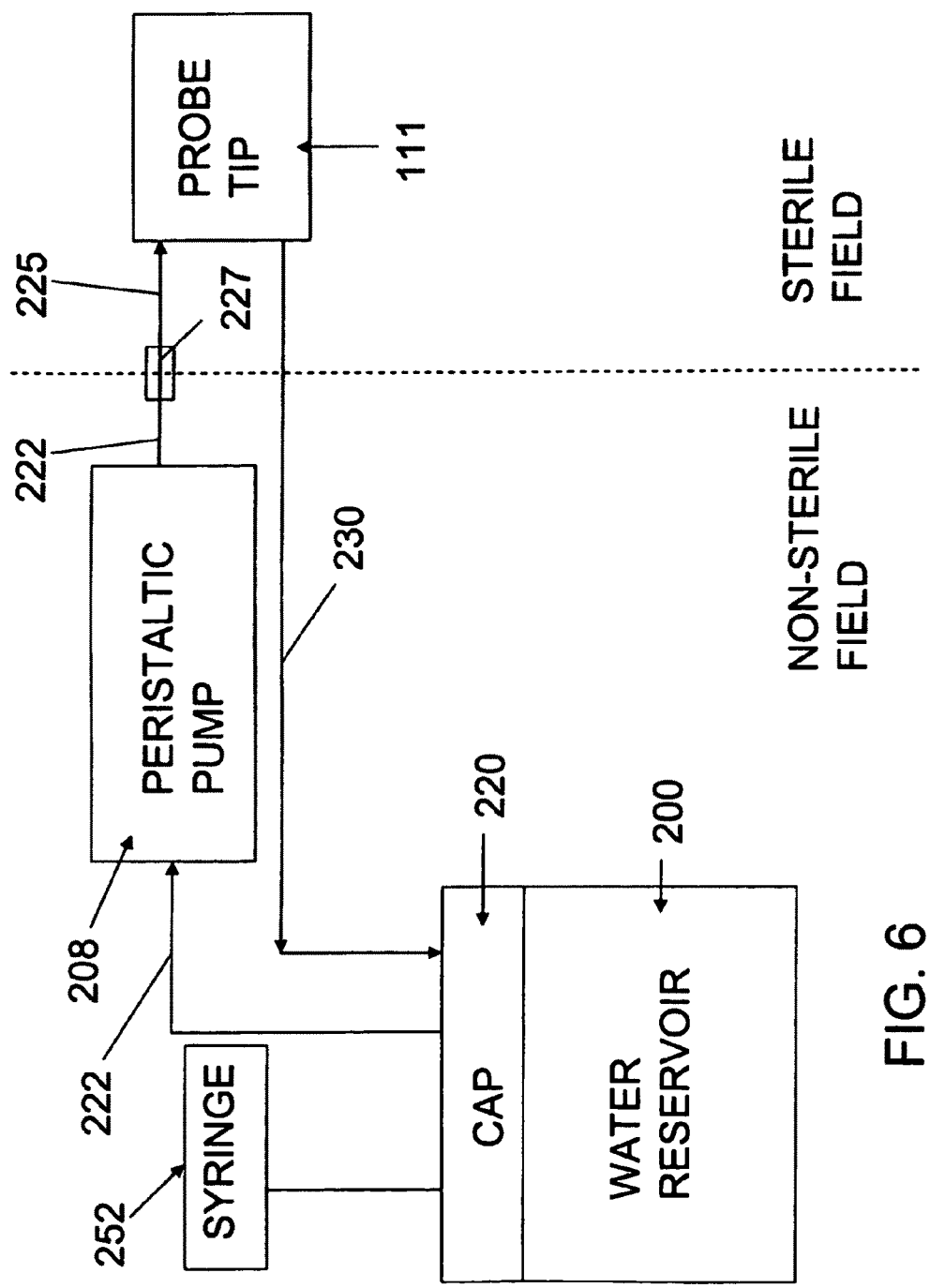
FIG. 6 illustrates a fluid recirculation system of the present invention which controls expansion of the bolus of the laparoscopic probe and also provides cooling to the transducer.

The present invention contains components that work together both inside and outside the sterile fields during the procedure. For instance a water reservoir 200 is placed under a conventional chiller which is located outside the sterile field as shown in FIG. 6. However, the degassed water inside the reservoir 200 remains sterile because it only passes through a sterile environment. The inside of the tubing is sterile thus the use of a non-sterile peristaltic pump 208 maintains the sterility of the water. After passing through the pump 208, the tubing enters the sterile field surrounding the patient. The tubing is connected to the back of the probe and water is pumped through the water bolus 118 and back out to the water reservoir 200.

Figure 5A:
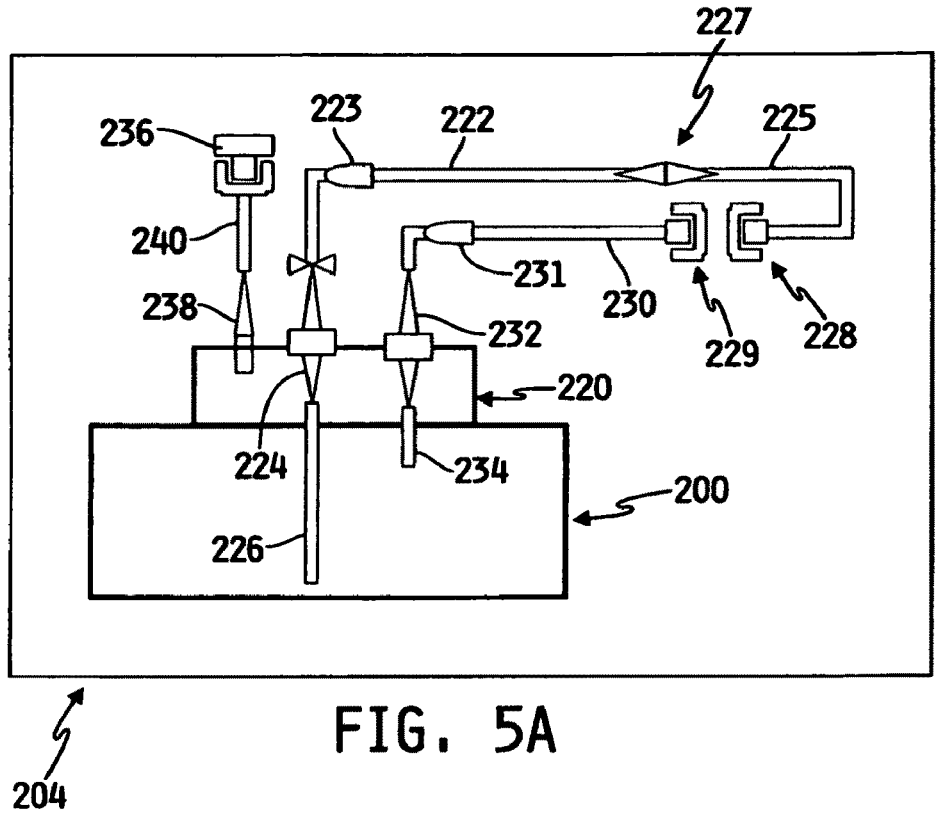
FIGS. 5A and 5B illustrate sterile kit packages for use in a fluid recirculation system of the present invention.
Figure 5B:
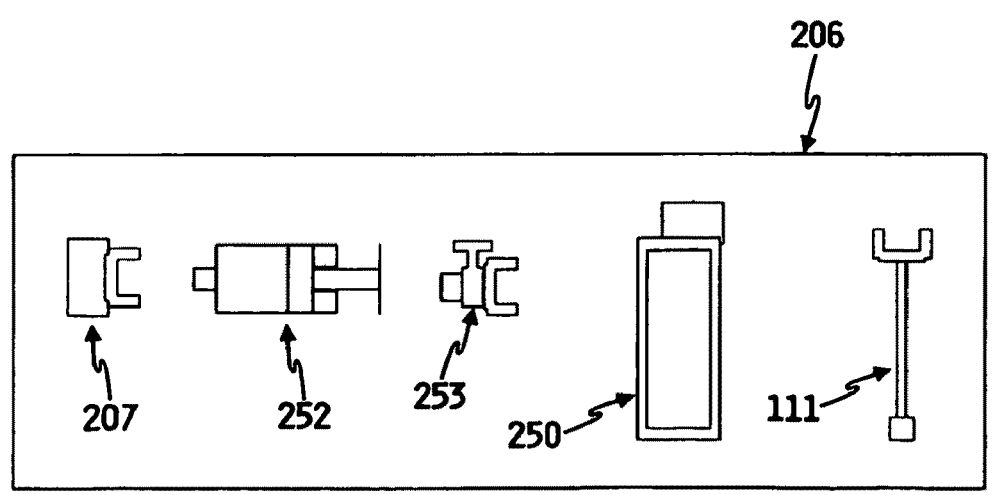

The reservoir 200 and tubing are illustratively produced as a first sterile kit in an enclosed, sealed package 204 with the tubing primed with sterile, degassed water as shown in FIG. 5A. A second sterile kit in an enclosed, sealed package 206 contains the components needed to prime the probe 111 and control the volume of water within the water bolus 118. The second kit 206 illustratively includes a female luer lock 207, a syringe 252, a stopcock 253, a filled 125 mL bottle 250 of distilled, degassed sterile water, sterile ultrasound coupling gel, o-rings and the removable probe tip 111 discussed earlier as illustrated in FIG. 5B. Since the probe tip 111 and everything that comes in contact with it must be sterile, both of these kits are sealed in sterile packaging 204, 206 (such as Tyvek material) and are gamma irradiated.

The water reservoir 200 acts as a heat sink in order to maintain the temperature of the transducer at safe operating levels (below approximately 30° C.). In addition, the water reservoir 200 is made from a rigid material in order to maintain a constant volume which is needed for control of the water bolus 118 height. The water bolus 118 provides a pressure release surface so the pressure within the water bolus 118 is close to zero gauge pressure. A peristaltic pump 208 illustratively creates either a vacuum or a positive pressure within the water reservoir 200 and the reservoir 200 must be able to withstand this pressure. The addition or subtraction of water to the water reservoir 200 results in changes to the water bolus 118 volume. Glass was illustratively chosen for the water reservoir 200 because of its rigid properties as well as the ability to maintain the degassed nature of the water compared to plastic (several months) over long periods of time (shelf life).

The water reservoir 200 is illustratively large enough, for example four liters in size, to act as a heat exchanger and remove heat from the water re-circulated to the probe. Therefore, a conventional active chiller does not need to be used in order to cool the water. Conventional chillers are typically not sterilized. Therefore, if the chiller was used, sterility of the water re-circulated to the pump would be broken. The large thermal mass provided with the water within reservoir 200 provides a suitable heat sink.

The preparation for a typical surgical procedure involves the following steps:
1) Placing all contents of the two kits 204, 206 within the sterile field.
2) Attaching the probe tip 111 to the probe
3) Priming the probe tip using a syringe and the additional bottle of degassed, distilled, sterile water.
4) Attaching the tubing to the main probe body 110.
5) Passing the water reservoir 200 out of the sterile field, hanging it below the chiller (or other desired location), and placing the pump compatible tubing 222 through the peristaltic pump 208.
6) Filling the syringe 252 with degassed, distilled, sterile water from bottle 250, attaching the stopcock 253 and passing the syringe 250 out of the sterile field. This syringe 252 is then attached to the third tube 240 coming out of the top cap 220 of the water reservoir 200 to control the bolus water volume.
7) Turn on the pump 208.
8) Remove all air bubbles from the probe tip housing.
9) Inflate the water bolus 118 and shape the bolus 118 for the treatment, see FIG. 2. The water bolus material 118 will "remember" the shape it took when it was last inflated.
10) Coat the water bolus 118 and tip 111 with ultrasound coupling gel.
11) Deflate the water bolus 118 for insertion into the trocar 60 using the syringe 252, now outside of the sterile field.
12) Position probe and adjust the water bolus 118 to obtain the desired transducer/probe positioning/coupling.

Referring to FIGS. 5A and 6, the water reservoir 200 illustratively provides a large volume of water, preferably about four liter(s) held within the glass container or reservoir 200. The reservoir 200 is sealed with a cap 220. A first tube section 222 is coupled to cap 220 by a connector 224. Connector 224 is coupled to an internal tube 226 having an open end located near a bottom of the reservoir 200. Illustratively, tube section 222 is special tubing made from C-Flex® by Masterflex® designed to fit within the pump 208. Tube 222 is coupled to another tube section 225 by connectors 227. An end 228 of tube 225 is configured to couple to a fitting on the probe tip 111. Tube section 230 includes an end 229 that couples to the other fitting of probe tip 111. Tube section 230 extends from the probe tip 111 back to a second connector 232 on cap 220. Tube section 230 is coupled to an internal tube 234 located within reservoir 200 and provides return fluid to the reservoir 200 from the bolus 118. Illustratively, tube sections 226 and 234 extend more than half way down into the fluid within the reservoir 200. The water is degassed, distilled and sterile. If desired, the water could be deionized. In the illustrated embodiment, tube 226 is located near the bottom of reservoir 200. The bottom of reservoir 200 likely contains the coolest water and is spaced apart from any air in the reservoir 200 that collects at the top of reservoir 200 near cap 220. As discussed above, the last few feet of the end portions of tubes 225 and 230 remain inside the sterile field (see FIG. 6) while the remaining components of the kits are passed outside the sterile field. A syringe 252 is configured to be coupled to connector 236 which is in turn, coupled to cap 220 by a connector 238 and a tube section 240. Normally open pinch clamps 223 and 231 are coupled to tubes 222 and 230, respectively. If needed, pinch clamps 223 and 231 and be closed to stop the flow of water therethrough. For instance, if the surgeon needs to replace the probe tip 111, the surgeon first turns the pump off, then pinch the clamps 223 and 231 can be closed to seal the tubes 222 and 230, respectively.

As discussed above, before the tube sections 225 and 230 are coupled to the probe tip 111, the probe tip is first primed using a syringe 252 and fluid from a container 250 located in kit 206. The bolus 118 is filled with the sterile water and the syringe is also filled or loaded with sterile water and transferred outside the sterile field and connected to connector 236 to control the expansion of bolus 118 from outside the sterile field.

The prediction on the size of the reservoir 200 required for adequate cooling is based on heat transfer from a probe [output level at maximum, TAP(total acoustic power)=39 W] an provides a conservative estimate of heating for a volume of water starting at room temperature (25 C).

Question: How many cycles (15 minutes HIFU ON and 2 minutes HIFU OFF) can 3.2 L of water starting at room temperature (25 C) withstand before reaching 30 C? Theoretical Prediction based on heat capacity of the water: 2.5 cycles to raise the temperature to 30 C.

$$\Delta T = Pt/(c\rho V)$$

Where the variables are defined as:
P=power (assume efficiency of transducer is 50% thus this is equal to TAP)
V=volume of the water reservoir
t=time
c=specific heat of water
p=density of water
ΔT=change in temperature
Experiment: 4 cycles were completed before raising the temperature of the water to 30 C (similar results were found for a second experiment).
Thus a gallon (3.8 L) of water at or below room temperature should suffice to cool the probe adequately for a procedure of reasonable length.

Figure 7:
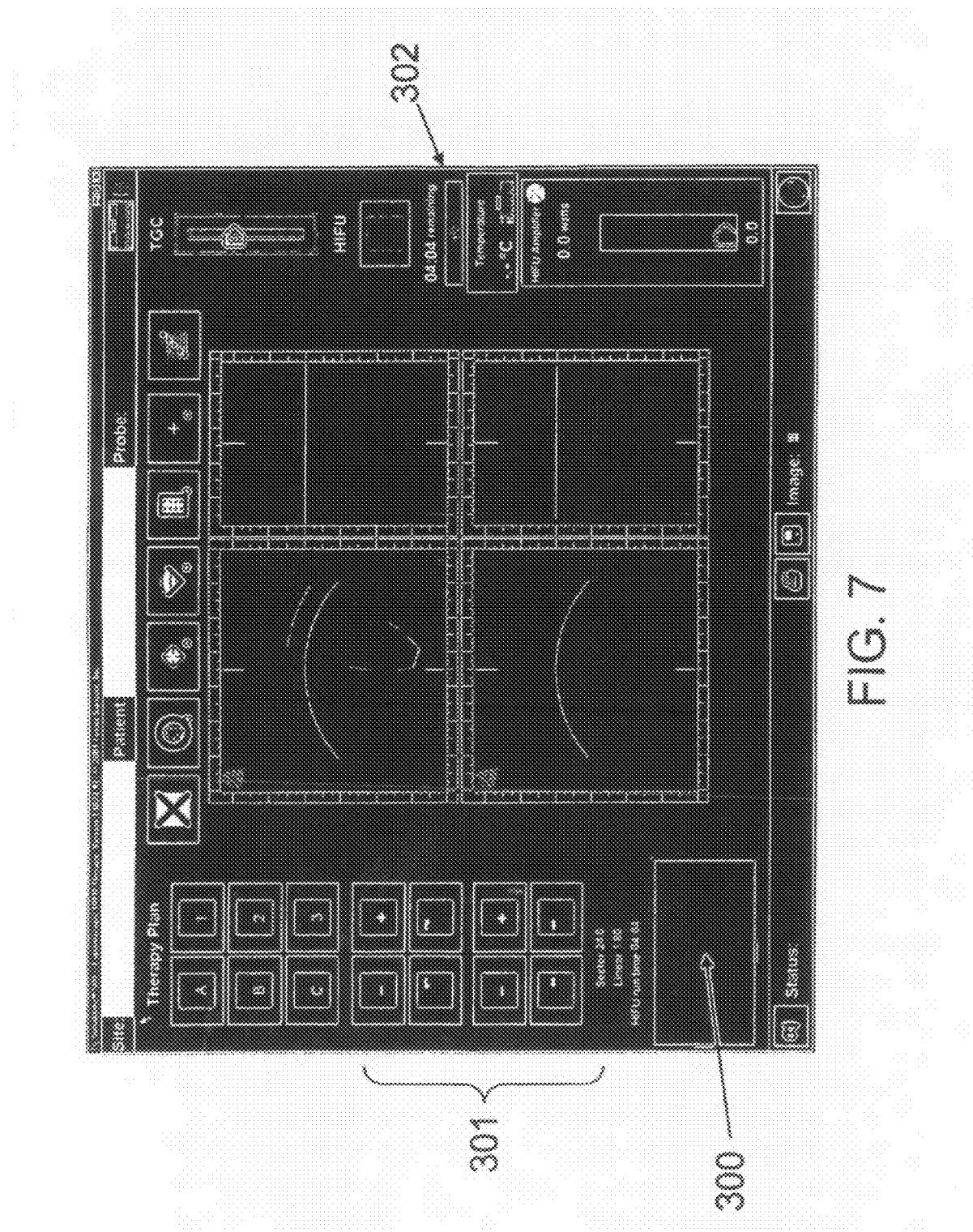
FIG. 7 is a sample screen shot for planning a HIFU Treatment.

Upon completion of the above steps the user plans and performs the HIFU treatment using software running on the Sonablate® 500 system connected to the laparoscopic probe 90. The physician uses the real time image capability of the laparoscopic probe to aid in the final placement of the probe. When the positioning is complete, an articulated arm holding the probe 90 is locked into place. The physician judges a real time image in both sector (rotating side to side transverse to the probe axis) and linear (back and forth along probe axis) motion ("bi-plane" images). Depending on the positioning and physician preference, either the linear or sector image may be chosen or the physician may alternate between the two. After physically moving the probe, fine tuning to the position of the treatment region is achieved by moving the treatment region using software controls 301. This adjusts the position of transducer 100 within the probe housing 135 resulting in fine tuning of the tissue treatment area. FIG. 7 displays an illustrated user interface with the treatment zones moved from the default center positions.

Once the treatment zone is positioned and resized by the physician to cover the desired tissue region (for example, a tumor), the HIFU Treatment is started and the probe begins to apply HIFU Therapy within the chosen region. The transducer trajectory is calculated by a series of algorithms that permit it to cover the entire treatment zone in a pattern illustrated in FIGS. 8A-8C. The trajectory is also designed to ensure constant equal trace spacing, meaning the spacing between the lines of the trajectory is substantially uniform throughout the region.

Figure 8C:
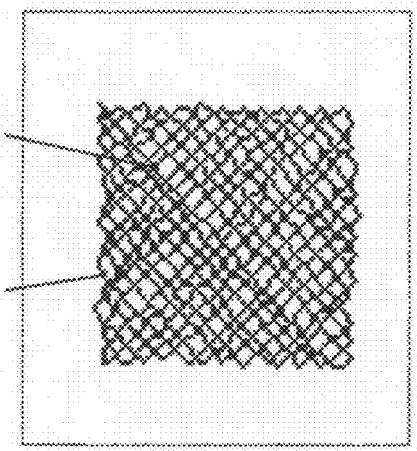
FIGS. 8A-8C illustrate a treatment path along which the transducer is moved by the controller and drive mechanisms to treat a treatment zone.
Figure 8B:
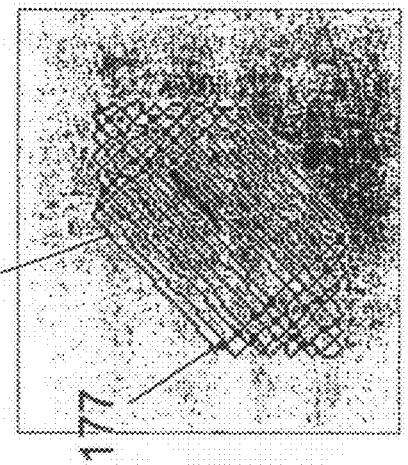
Figure 8A:
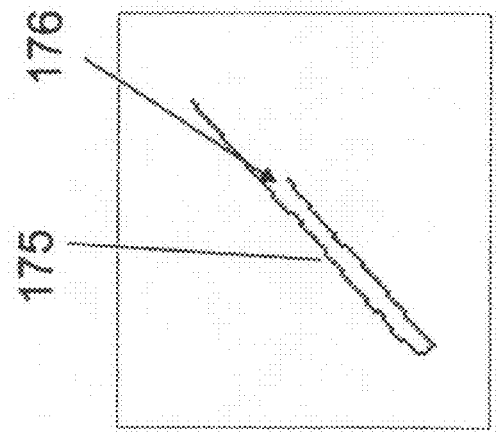

FIGS. 8A-8C illustrate an exemplary pattern of HIFU Therapy application during HIFU Treatment with the laparoscopic probe. FIG. 8A is representative of the treatment path 175 soon after the start of the treatment. FIG. 8B is representative of the treatment path 175 midway, and FIG. 8C is representative of the treatment path 175 near the end. The tracings depict the linear (vertical) and the sector (angular) positions of the transducer 100 during the treatment. This user feedback is continuously updated during the treatment. Once the treatment starts, the transducer is continuously moving at constant speed and continuously applying HIFU to the tissue treatment area.

Figure 9:
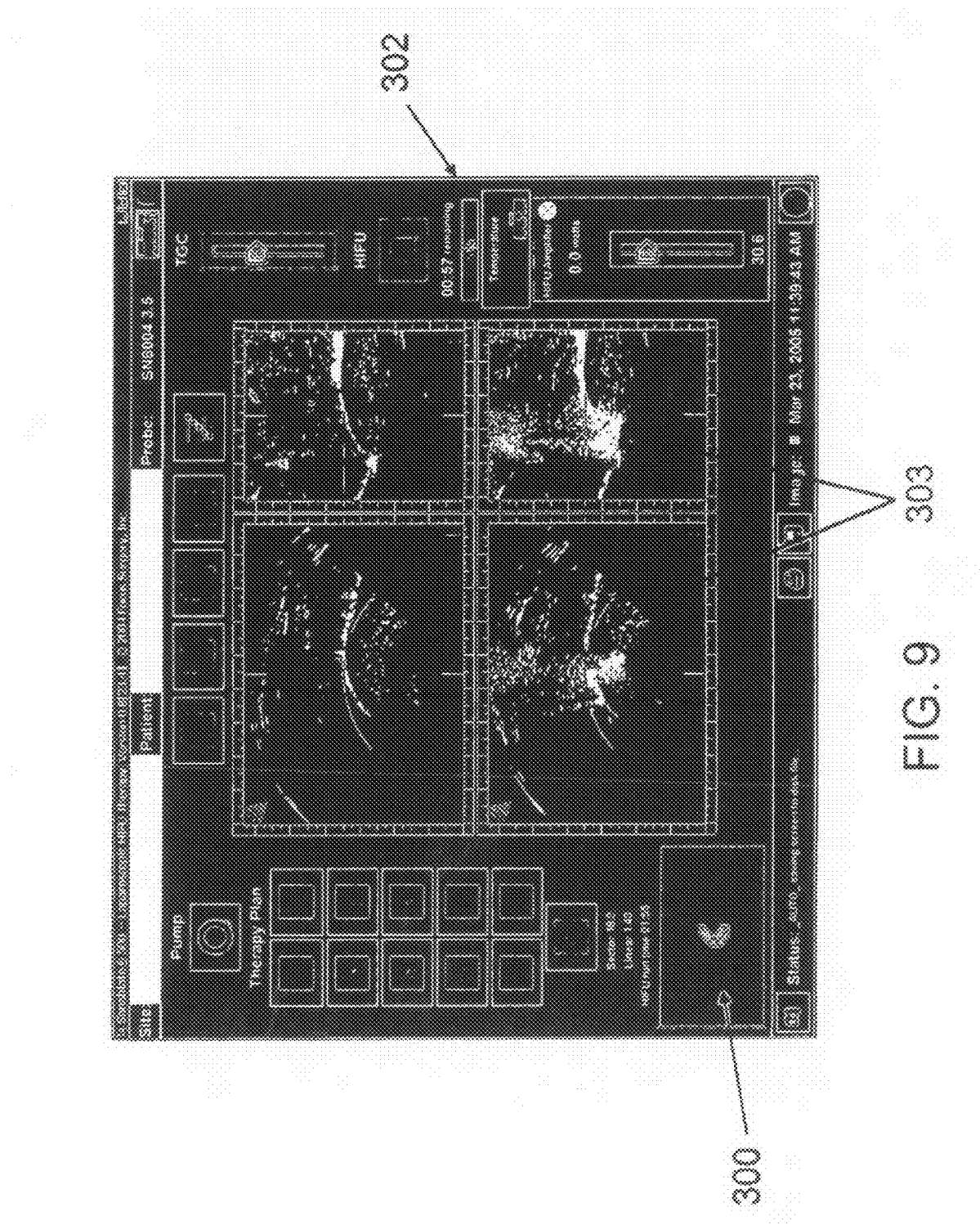
FIG. 9 is a screen shot illustrating a sample procedure in accordance with an illustrated embodiment of the present invention.

FIG. 9 illustrates an image update taken with the imaging transducer during treatment. The upper panels show the tissue before application of HIFU Treatment. The lower panels display the images acquired during the HIFU Treatment. Treatment progress may be gauged by the tracing in position 300 the lower left corner, by the time remaining 302 along the right side of the screen, and by the HIFU-induced echogenic tissue changes visible in the "after" image 303.

The screenshot shown in FIG. 9 was taken about half way through a HIFU Treatment. In the bottom left HIFU run time indicates that this particular treatment has lasted 1 minute and 55 seconds and the time remaining 302 (on the right side) shows 57 seconds. Once the HIFU Treatment is complete, the water reservoir 200 and associated tubing along with any components of the kits (including the removable probe tip 111) that were used are discarded.

The treatment algorithms of the present invention are designed to substantially fill a treatment zone or region selected by the physician. Often, these treatment zones or regions are not symmetrically shaped. Software of the present invention controls a controller 93 to move the transducer 100 back and forth in the direction of double headed arrow 106 in FIG. 1 and to rotate the transducer about its axis 107 as illustrated by arrow 108 in FIG. 1 to provide a continuous treatment path within the selected treatment region. As illustrated in FIGS. 8A, 8B and 8C, the transducer moves at constant speed, (about 1-2 mm/sec.) to provide spacing between the treatment path followed by the transducer of about 1.5-2.0 mm. The algorithm is designed to keep the spacing between adjacent portions of treatment path 175 substantially constant as illustrated at 176 in FIG. 8A and to cross or intersect a previous portion of the treatment path 175 at an angle as close to 90 degrees as possible (see, for example, intersections 177 in FIGS. 8B and 8C) to avoid retracing the path 175. This pattern of path spacing at essentially 90 degree crossing provides a more uniform heat distribution with respect to depth inside the treatment region. When path 175 hits a boundary edge of a treatment zone defined by a physician, the path 175 changes directions at an angle of about 90°. In FIGS. 8A-8C, the physician defined a square treatment zone best shown by the filled zone in FIG. 8C. It is understood, however, that the treatment regions may be defined in any desired shape (typically rectangular) and are often not square.

In the illustrated HIM Therapy, the trajectory stays within bounds parallel to the trajectory path. The bounds limit is a floating-point value specified in millimeters and placed in a property file. Default is 1.5 millimeters, checked every 200 milliseconds, but not checked within 200 milliseconds of an image update, end of move, or corrective action sweeps. Upon receiving a $2^{nd}$ sequential out-of-bounds reading, the RF power is turned off and the probe is commanded to perform a linear and sector sweep. A level 1 corrective action taken flag will be set and therapy resumed. Upon reaching the end of the current move, the corrective action flag will be reset. If two consecutive out-of-bounds readings are again detected before the end of the move, the probe is homed, a level 2 corrective action flag is set, and therapy will continue. If two consecutive out-of-bounds readings are again detected before the move is completed, therapy is stopped. This "intelligent" checking is incorporated to reduce treatment interruptions due to single errors, allows for graceful degradation and minimizes physician interaction with the mechanical aspects of the probe. If the probe, even after recovery efforts, still fails, this provides an indication of tissue blocking the transducer, or a mechanical problem.

During a single move, a check is made to make sure the distance to the destination is decreasing. The required decrease value is a floating-point value is specified in millimeters and placed in a property file. Default is 0.2 millimeters, checked every 400 milliseconds. Not checked within 200 milliseconds of an image update. Corrective action similar to paragraph [0050] will be taken in the event of errors.

After an individual move starts, the controller 93 makes sure it finishes within the move time specified in the trajectory list +/−25% and +/−500 milliseconds. Tolerance values are placed in a property file. The controller 93 tracks the move number and makes sure the move number increments properly. Checked every 200 milliseconds. Corrective action similar to paragraph [0050] will be taken in the event of errors.

A data validation check is performed at the start of therapy, after each image update, and after a pause therapy. The controller 93 makes sure that no move exceeds the maximum theoretical move time and no linear and sector data points are outside the therapy treatment area. If an error is found the controller 93 reconstructs the data structure and checks again. In the event of error, the trajectory data is assumed corrupted and therapy is stopped. The controller 93 makes sure that resume data points are within 1.5 millimeters of the therapy bounds, value placed in a property file.

A watchdog timer is reprogrammed to cut off RF output if it is not kicked at a 1 Hz rate. If the emergency stop button located on the Sonablate® 500 console is pressed, the controller 93 pauses therapy and display the emergency stop icon. The pump 208 is also stopped.

If the probe temperature goes into the yellow zone, the controller flashes the temperature icon and turns pump 208 on. The controller 93 stops therapy if in the red zone upon second sequential reading. The probe temperature is read once every 5 seconds. Illustratively, the yellow zone temperature ranges from 25 to 30° C. The red zone temperature is above 30° C.

If the reverse watts percent is greater than the maximum reverse watts percent, the controller 93 stops therapy on a second sequential reading. Read once a second. Absolute value watt limits will also be checked to avoid false alarms at low power (10-15 watts). No test within 500 milliseconds of an RF on/off transition or power output change.

If the RF power exceeds the probe maximum for two consecutive readings, the controller 93 stops therapy. Median power readings are used based on readings checked once per second. No test within 500 milliseconds of an RF on/off transition or power output change.

The controller 93 monitors the watchdog timer output to make sure it is following RF output commands. If detected, the controller 93 runs the code to put the watchdog timer back in the verification mode. Resume therapy. If additional errors detected, stop therapy.

The preceding paragraphs give an illustration of the built-in safety checks and error recovery algorithms designed mainly to turn the HIFU delivery OFF in the case of a failure, or to gracefully recover from a motor/transducer positions error due to probe tolerances, probe/tissue interactions, or probe failure.

The efficacy, performance, utility, and practicality of these newly developed Sonablate® Laparoscopic (SBL) probes and treatment methodologies was evaluated in-vivo using a pig model. Pre-selected kidney volumes (1 cm$^3$ to 18 cm$^3$) were targeted for ablation (including the upper and lower poles, and regions adjacent to the collective system and ureter), and treated laparoscopically with HIFU in a sterile environment using the SBL probes. Integrated ultrasound image guidance was used for probe positioning, treatment planning, and treatment monitoring. The kidneys were removed either 4 or 14 days post-HIFU, and the resulting lesions were compared to the treatment plan. Results indicate that HIFU can be used laparoscopically to ablate kidney tissue at a rate of approximately 1 to 2 cm$^3$/minute, even in highly perfused organs like the kidney. Results also indicate that treatment methodologies vary depending on the target location, intervening tissue, probe location, and port location.

The following provides an illustrative example of the treatment path generation software used to determine the transducer path based on a treatment plan/region arbitrarily selected by the physician:

```
% trajectory12
% rs v1.2 10/6/2004
clear
close all
% Notes:
% Results contained in the variable 'points', correctly ordered, in [mm, mm].
linsta=0;        %mm (0 to 25)
linsto=10;       %mm (25 to 50)
secsta=-5;       %deg (-45 to 3) (minimum 6 degree extent...)
secsto=5;        %deg (3 to 45)
fl=35;           %mm; focal length
sp=2;            %mm; spacing of traces; put in property file
gspeed=1.5;      %mm/s; global speed; put in property file
wstandoff=15;    %mm; water standoff; determine from 'rectal wall distance measurement'
plt1=1; %plot
plt2=1; %plot
lmax=linsto-linsta;             %mm; maximum linear travel
Vl=1.5;                         %mm/s; initial guess linear
amax=secsto-secsta)/360*(2*pi*fl);   %mm; maximum sector travel
```

-continued

```
at specified focal length
Va=1.5;                         %mm/s; initial guess angle
fe=12;                          %mm; focal extent
disp(' ');
disp(['Linear travel: ' num2str(lmax) ' mm.']);
disp(['Angular travel: ' num2str(amax) ' mm.']);
vincr=0.01; % velocity change
T=100;
t=linspace(0,T,1000); %s
tincr=0.02;
sperror=0.1;
d=1000;
wc=0;
while abs(d-sp)>sperror,
    x=rem(Va*t,2*amax);
    y=rem(Vl*t,2*lmax);
    for i=1:length(t),
        if x(i)>amax, x(i)=2*amax-x(i); end
        if y(i)>lmax, y(i)=2*lmax-y(i); end
    end
    % determine 1st slope...
    m1=(y(2)-y(1))/(x(2)-x(1));
    c1=0;
    % now find the next sets of points at which the slope is the same as m1...
    m2=0;
    count=3;
    while y(count) > y(2),
        count=count+1;
    end
    count=count+1;
    % m2=(y(count+1)-y(count))/(x(count+1)-x(count));
    m2=m1;
    c2=y(count+1)-m2*x(count+1);
    x2=x(count);
    y2=y(count);
    % now find the spacing between these two lines...
    mp=-1/m1;
    xd=c2/(mp-m2);
    yd=mp*xd;
    d=sqrt(xd^2+yd^2);
    % show results for current iteration...
    if plt1==1,
        figure(1);
        clf;
        plot(x,y,'.');
        hold on;
        line([0 amax], [0 0],'Color',[1 0 0], 'LineWidth',2);
        line([0 amax],[lmax lmax],'Color',[1 0 0],'LineWidth',2);
        ? line([0 0],[0 lmax],'Color',[1 0 0],'LineWidth',2);
        axis([-20 amax+20-20 lmax+20]);
        axis equal
        line([xd],[0 yd],'Color',[0 1 0],'LineWidth',2);
        plot(xd,yd,'go');
        plot(x2,y2,'mo');
        drawnow;
    end
    Va=Va+vincr;
    wc=wc+1;
end
Va=Va-vincr;
% Now we know the parameters that will generate parallel lines Vl
and Va...
% disp([wc sp d Vl Va]);
% Find the points in the correct order...
    tp=[0 tincr tincr*2];
    count=2;
    points=[0 0];
    done=0;
    while done==0,,
        xp=rem(Va*tp,2*amax);
        yp=rem(V1*tp,2*lmax);
        for i=1:3,
            if xp(i)>amax, xp(i)=2*amax-xp(i);end
            if yp(i)>lmax, yp(i)=2*lmax-yp(i);end
        end
        m1x=xp(2)-xp(1);
        m2x=xp(3)-xp(2);
        m1y=yp(2)-yp(1);
        m2y=yp(3)-yp(2);
        if sign(m1x) ~= sign(m2x),
            points(count,1:2)=[xp(2) yp(2)];
            count=count+1;
        end
        if sign(m1y) ~=sign(m2y),
            points(count,1:2)=[xp(2) yp(2)];
            count=count+1;
        end
        tp=tp+tincr;
        % check to see when we are done, be checking if the last point is
        close to any of the previous points...
            mindelta=1000;
            for i=1:count-2,
                delta=sqrt((points(count-1,1)-points(i,1))^2+(points
(count-1,2)-points(i,2))^2);
                if delta<mindelta, mindelta=delta; end
            end
            if mindelta<(sp-sperror), done=1; end
        end
    % shift points...
    points(:,1)=points(:,1)+(secsta/360*2*pi*fl);
    points(:,2)=points(:,2)+linsta;
    if plt2==1,
        figure(2);
        clf;
        plot(points(:,1),points(:,2),'bo'); hold on
        plot(points(:,1),points(:,2),'b');
        plot(points(1,1),points(1,2),'go');
        plot(points(count-1,1),points(count-1,2),'ro');
        axis(-35 35 -5 55]);
        xlabel('Angular distance in focal plane [mm]');
        ylabel'Linear distance [mm]');
        axis equal;
    end
    % determine the total time and travel distance...
    dtot=0;
    for i=1:count-2,
        dtot=dtot+sqrt((points(i+1,1)-points(i,1))^2+(points
(i+1,2)-points(i,2))^2);
    end
    disp(' ');
    V=(secsto-secsta)/360*pi*((fl+fe/2)^2-wstandoff^2)*lmax/1000;
    dispa([Total travel: ' num2str(dtot) ' mm']);
    disp(['Therapy time: ' num2str(dtot/gspeed) ' s ('num2str(dtot/
gspeed/60) ' min).']);
    disp(['Volume treated: ' num2str(V) ' cm^3 (' num2str(V/(dtot/
gspeed/60)) ' cm^3/min), with a' num2str(wstandoff) ' mm
water standoff.']);
    disp(['Focal length: ' num2str(fl) ' mm.']);
    disp(['Line segments: ' num2str(count-2)]);
    disp(['Line spacing: ' num2str(sp) 'mm.']);
    disp(['Linear speed: ' num2str(gspeed) ' mm/s.']);
    disp(' ');
```

It is understood that the above example is illustrative only and that other control software may be used in accordance with the present invention.

Although the invention has been described in detail with reference to certain illustrated embodiments, variations and modifications exist within the spirit and scope of the invention as described and defined in the following claims.

The invention claimed is:

1. An apparatus for treating a targeted area of tissue, the apparatus comprising:

a probe having a probe tip and a housing formed to include an aperture therein, a transducer coupled to the probe, the transducer being configured to emit ultrasound energy through the aperture in the housing to provide HIFU Therapy to the targeted area, the probe tip being positionable to provide HIFU Therapy to the targeted area, an expandable membrane coupled to the housing, the membrane being configured to expand in a treatment direction to acoustically couple the transducer to the targeted area; and a controller configured to move the transducer to provide HIFU Therapy within a preselected treatment area, wherein the controller moves the transducer so that HIFU energy is provided along a treatment path in the preselected treatment area at about a constant speed, wherein the controller moves the transducer so that the distance between adjacent portions of the treatment path are substantially constant, and wherein the controller moves the transducer so that HIFU energy is provided to intersect a portion of the treatment path.

2. The apparatus in claim 1, wherein the controller moves the transducer so that HIFU energy is provided along a treatment path at a constant speed of about 1 to 2 millimeters per second.

3. The apparatus in claim 1, wherein the controller is configured to move the transducer back and forth along a longitudinal axis of the probe.

4. The apparatus in claim 1, wherein the controller is configured to rotate the transducer about its axis.

5. The apparatus in claim 1, wherein the controller moves the transducer to maintain a distance between adjacent portions of the treatment path of about 1.5 to 2.0 millimeters.

6. The apparatus in claim 1, wherein the controller moves the transducer so that the HIFU energy stays within a bounds limit parallel to the treatment path.

7. The apparatus in claim 1, wherein the controller moves the transducer so that the HIFU energy intersects a portion of the treatment path at an angle of about 90 degrees.

8. The apparatus in claim 1, wherein the controller moves the transducer so that the HIFU energy changes directions at an angle of about 90 degrees when the treatment path reaches an edge of the preselected treatment area.

9. The apparatus in claim 1, wherein the controller contains a watchdog timer that is reprogrammed to cut off RF output if the timer is not reset at a 1 Hz rate.

10. A sterile apparatus for treating a targeted area of kidney or liver tissue, the apparatus comprising:

a probe having a probe tip having a housing formed to include an aperture therein, a transducer coupled to the probe, the transducer being configured to emit ultrasound energy through the aperture in the housing in a treatment direction to provide HIFU Therapy to the targeted area, the probe tip being positionable approximate to the targeted area, an expandable bolus coupled to the housing, the bolus being configured to expand in the treatment direction to couple the transducer to the targeted area acoustically; and a controller configured to provide HIFU Therapy to the targeted area to substantially fill a treatment region having a boundary selected by a physician, the controller moving the transducer along a continuous treatment path within the treatment region and maintaining a distance between adjacent portions of the treatment path substantially constant, the controller also moving the transducer so that the treatment path intersects a previous portion of the treatment path at substantially a 90 degree angle, when possible, to avoid retracing the previous portion of the treatment path.

* * * * *